Figure 1:
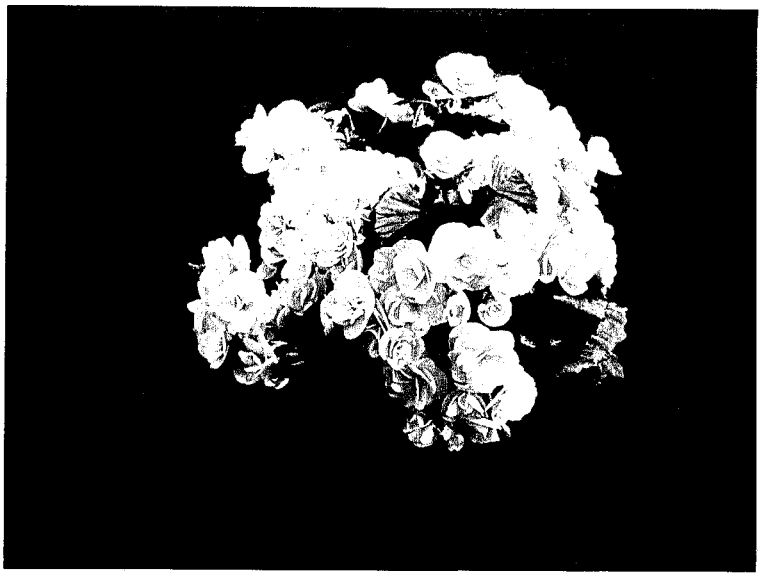

United States Patent [19]

Man

[11] Patent Number: Plant 7,398

[45] Date of Patent: Dec. 18, 1990

[54] BEGONIA CULTIVAR MANDERIJN

[75] Inventor: Jan Man, Amstelveen, Netherlands

[73] Assignee: Gebr. Man C.V., Aalsmeer, Netherlands

[21] Appl. No.: 329,119

[22] Filed: Mar. 27, 1989

[51] Int. Cl.[5] ..... A01H 5/00

[52] U.S. Cl. ..... Plt./68

[58] Field of Search ..... Plt./68

[56] References Cited

U.S. PATENT DOCUMENTS

P.P. 5,746 5/1986 Rohde ..... Plt. 68

*Primary Examiner*—James R. Feyrer

*Attorney, Agent, or Firm*—Renner, Otto, Boisselle & Sklar

[57] ABSTRACT

A Begonia plant named Manderijn characterized by its orange-salmon double sterile flowers up to 5 cm. in diameter, medium size dark green foliage, vigorous upright, self-branching mounded plant, year round flowering, and the ability to maintain good quality flowers for long periods of time.

1 Drawing Sheet

The present invention relates to a new and distinctive cultivar of Begonia plant, botanically known as Begonia hiemalis, Fotsch, and known by the cultivar named Manderijn.

This new cultivar was discovered by me as a mutation of the cultivar Karita, disclosed in U.S. Plant Pat. No. 5,746, and was observed in a group of 13 cm. flowering plants of Karita in a cultivated area.

Asexual reproduction by stem and/or leaf cuttings has reproduced the unique features of this new cultivar through successive propagations.

The following characteristics distinguish Manderijn from both its parent Karita and grandparent Kascade (unpatented) as well as other begonias commercially known and used in the floriculture industry:

1. Manderijn is later flowering than Karita and has more intensive green colored leaves. Also, Manderijn has orange-salmon colored flowers, whereas Karita has light pink colored flowers. All other growth and propagation habits of Manderijn are the same as Karita.

2. Manderijn has more intensive green colored leaves than Kascade. Also, Manderijn has orange-salmon colored flowers, whereas Kascade has light pink colored flowers.

3. In comparison to Ilona (unpatented), Manderijn has more intensive flowers that are more double and have a larger diameter than Ilona. Also, Manderijn forms larger leaves and is more vigorous than Ilona, and produces less flowers per plant than Ilona.

4. In comparison to Enchantment, disclosed in U.S. Plant Pat. No. 6,427, Manderijn has more intensive orange colored flowers that are less double than Enchantment. Also, the growth habit of Manderijn is more compact than Enchantment.

5. In comparison to Bolero, Manderijn has a more salmon-orange, less filled and larger diameter flower than Bolero. Also, the leaves of Manderijn have a green-reddish color whereas the leaves of Bolero are green, and Manderijn is less compact than Bolero.

6. In comparison to Improved Schwabenland Orange, Manderijn is a double flowering type whereas Improved Schwabenland Orange is single flowering. Also, Manderijn is more compact and the leaf color is more dark green than that of Improved Schwabenland Orange.

Figure 2:
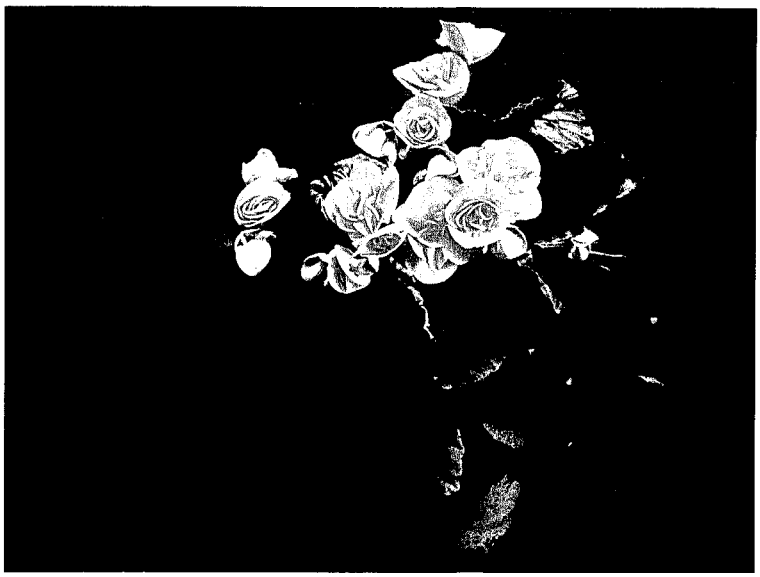

Referring now more particularly to the accompanying drawing:

FIG. 1 is a colored photograph taken November 1989 illustrating in perspective view the overall appearance of the cultivar Karita, showing the colors as true as it is reasonably possible to obtain in a colored reproduction of this type; and FIG. 2 is a colored photograph taken in November 1989 illustrating in perspective view the overall appearance of the cultivar Manderijn, showing the colors as true as it is reasonably possible to obtain in a colored reproduction of this type.

The following is a detailed description of my new cultivar Manderijn based on plants produced under commercial practices in greenhouses in Amstelveen, The Netherlands, and Oberlin, Ohio, and grown in 10 cm. plastic pots. Color references are made to The Royal Horticultural Society Colour Chart, except where general color terms of ordinary dictionary significance are used.

Parentage: Manderijn is a mutation of begonia cultivar Karita, induced by giving X-ray doses of 2 KRAD to 250 top cuttings of Karita. After pinching the irradiated cuttings two times, 1,000 top cuttings were taken and brought into flower where possible. Out of these flowering plants, the parent of Manderijn was picked, and after two years of selection and cloning work, Manderijn was developed from this single parent plant.

Propagation:

(A) *Type cutting.*—Normal production is from top cutting. However, propagation by leaf cuttings is possible. Cuttings are initially placed under plastic tents.

(B) *Time to root.*—15 days at 24° C. in summer and in winter under HID-lights.

(C) *Rooting habit.*—Fibrous, dendritic, and abundant.

(D) *Time for shoot development.*—For leaf cuttings with 2 cm. long shoots, a growth period of nine weeks is necessary.

Plant description:

(A) *Form.*—Compact, internodes relatively closely, vigorous self-supporting, herbaceous.

(B) *Habit of growth.*—Upright, self-branching, rapid growth, dark green-reddish foliage. The plant is considered to be of medium height.

(C) *Foliage.*—(1) Size: leaves vary in length with age from 6 to 10 centimeters and in width from 8 to 11 cm. for plants in 12 cm pots. (2) Shape: generally pointed at the top and open at the base. The incisions are of bi-crenate type, while there is only little undulation. (3) Texture: crisp to firm, top more soft. (4) Color: upper side darker than light green 147A; lower side reddish-green; glossiness of lower side is strong.

Flowering description:

(A) *Flowering habit.*—Flowering generally occurs in terminal racemes with the inflorescence having 6–8 flowers. Once flowering begins, it continues at each succeeding node.

(B) *Natural flowering season.*—Flowering is indeterminate, with flowering occurring in all seasons.

(C) *Flower buds.*—Round to slightly oval, each 15 mm. in diameter prior to opening with outer petals being 48B carmin.

(D) *Flowers borne.*—On strong self-supporting pedicels originating from vigorous peduncles giving the appearance of a strong plant.

(E) *Quality.*—Considered to be an average floriferous cultivar, but flowers are uniformly placed to give an excellent contrast between flowers and foliage.

(F) *Flower size.*—Double, sterile flowers up to 5 cm. in diameter.

(G) *Overall appearance of flower color.*—38A orange-salmon.

(H) *Petals.*—(1) Shape: Outer nearly round, inner ovate. (2) Color of outer petal: edge of upper side 48B carmin; middle of upper side 43B bright reddish; middle of lower side 48B carmin. (3) Color of inner petals: edge of upper side 38A orange-salmon; middle of upper side 38A orange-salmon; middle of lower side 38B orange-pink. (4) Number of petals: for flower of average age, 13–15. (5) Incisions: not present on the petals.

(I) *Reproduction organs.*—None, Manderijn is a sterile tripoloid cultivar (4N×2N).

I claim:

1. A Begonia plant named Manderijn, as described and illustrated, having orange-salmon, double, sterile flowers up to 5 cm. in diameter; medium size dark green foliage; vigorous and upright growing; self-branching; year round flowering; and the ability to maintain good quality flowers for long periods of time.

* * * * *